US012576232B2

(12) United States Patent
Jung

(10) Patent No.: US 12,576,232 B2
(45) Date of Patent: *Mar. 17, 2026

(54) VENTILATOR SYSTEM AND MEDICAL GAS DELIVERY SYSTEM

(71) Applicant: YUAN ZE UNIVERSITY, Taoyuan City (TW)

(72) Inventor: Guo-Bin Jung, Taoyuan County (TW)

(73) Assignee: YUAN ZE UNIVERSITY, Taoyuan City (TW)

( * ) Notice: Subject to any disclaimer, the term of this patent is extended or adjusted under 35 U.S.C. 154(b) by 976 days.

This patent is subject to a terminal disclaimer.

(21) Appl. No.: 17/715,163

(22) Filed: Apr. 7, 2022

(65) Prior Publication Data

US 2022/0323710 A1 Oct. 13, 2022

(30) Foreign Application Priority Data

Apr. 9, 2021 (TW) ................................. 110112888

(51) Int. Cl.
*A61M 16/10* (2006.01)
*A61M 16/12* (2006.01)
(Continued)

(52) U.S. Cl.
CPC ............ *A61M 16/10* (2013.01); *A61M 16/12* (2013.01); *A61M 16/16* (2013.01); *C25B 15/02* (2013.01);
(Continued)

(58) Field of Classification Search
CPC .... A61M 16/12; A61M 13/003; A61M 16/16; A61M 2016/0021; A61M 2016/1025;
(Continued)

(56) References Cited

U.S. PATENT DOCUMENTS

| | | | |
|---|---|---|---|
| 6,439,229 B1 * | 8/2002 | Du | A61M 16/026 |
| | | | 128/204.26 |
| 10,364,503 B2 * | 7/2019 | Jung | A61K 33/00 |

(Continued)

FOREIGN PATENT DOCUMENTS

| | | |
|---|---|---|
| CN | 209873126 U | 12/2019 |
| CN | 112336953 A | 2/2021 |

(Continued)

OTHER PUBLICATIONS

The English Machine translation of WO9831282A1 is translated via the US Fit database on Dec. 26, 2024 (Year: 1998).*

(Continued)

*Primary Examiner* — Justine R Yu
(74) *Attorney, Agent, or Firm* — Li & Cai Intellectual Property (USA) Office

(57) ABSTRACT

A medical gas delivery system and a ventilator system are provided. The medical gas delivery system includes an electrolytic gas generation device, a delivery device, and a control unit. The electrolytic gas generation device is used to generate a first gas and a second gas. The delivery device is in fluid communication with the electrolytic gas generation device, and is used to transport a medical gas. The medical gas includes at least one of the first gas and the second gas. The control unit is electrically connected with the electrolytic gas generation device and the delivery device, so as to control a component ratio of the medical gas.

13 Claims, 3 Drawing Sheets

(51) Int. Cl.
| | | |
|---|---|---|
| *A61M 16/16* | (2006.01) | |
| *C25B 15/02* | (2021.01) | |
| *A61M 13/00* | (2006.01) | |
| *A61M 16/00* | (2006.01) | |

(52) U.S. Cl.
CPC ... *A61M 13/003* (2013.01); *A61M 2016/0021* (2013.01); *A61M 16/024* (2017.08); *A61M 2016/1025* (2013.01); *A61M 2202/0208* (2013.01); *A61M 2202/0216* (2013.01); *A61M 2205/3331* (2013.01); *A61M 2210/1067* (2013.01)

(58) Field of Classification Search
CPC .. A61M 2202/0208; A61M 2202/0216; A61M 2205/3331; A61M 2210/1067; A61M 16/021–024; A61M 16/10–102; C25B 15/02
USPC ............. 128/202.26; 600/543, 532, 309, 367
See application file for complete search history.

(56) References Cited

U.S. PATENT DOCUMENTS

| | | | | |
|---|---|---|---|---|
| 2011/0180063 A1* | 7/2011 | Hunsicker | ......... | A61M 16/0051 128/200.14 |
| 2013/0104896 A1* | 5/2013 | Kimm | ................. | A61M 16/024 128/204.23 |
| 2015/0090264 A1* | 4/2015 | Dong | ................... | A61M 16/026 128/204.23 |
| 2015/0107588 A1* | 4/2015 | Cheung | ............... | A61M 16/026 128/203.14 |
| 2015/0190604 A1* | 7/2015 | Lin | .................... | A61M 16/0833 128/202.26 |
| 2015/0359979 A1* | 12/2015 | Nagata | ................. | A61M 11/005 128/200.14 |
| 2018/0133248 A1* | 5/2018 | Caplan | .................... | A61P 39/00 |
| 2018/0135948 A1 | 5/2018 | Stone et al. | | |
| 2018/0154102 A1* | 6/2018 | Selander | ............. | A61M 16/024 |
| 2018/0344958 A1* | 12/2018 | Heinonen | .............. | G16H 40/40 |
| 2020/0155777 A1* | 5/2020 | Acker | ............... | A61M 16/0051 |

FOREIGN PATENT DOCUMENTS

| | | | | | | |
|---|---|---|---|---|---|---|
| DE | 102013003721 A1 | * | 9/2014 | ........ | A61M 16/1005 |
| FR | 3091822 A1 | * | 7/2020 | ........... | A61M 16/12 |
| TW | I634941 B | | 9/2018 | | |
| WO | WO-9831282 A1 | * | 7/1998 | ........... | A61M 16/12 |
| WO | WO-2021022921 A1 | * | 2/2021 | ........... | A61M 16/00 |

OTHER PUBLICATIONS

The English Machine translation of FR3091822A1 is translated via the US Fit database on Dec. 29, 2024 (Year: 2020).*
The English Machine translation of DE102013003721A1 is translated via the US Fit database on Dec. 29, 2024 (Year: 2014).*
The English Machine translation of WO2021022921A1 is translated via the US Fit database on Jan. 14, 2025 (Year: 2021).*

* cited by examiner

VENTILATOR SYSTEM AND MEDICAL GAS DELIVERY SYSTEM

CROSS-REFERENCE TO RELATED PATENT APPLICATION

This application claims the benefit of priority to Taiwan Patent Application No. 110112888, filed on Apr. 9, 2021. The entire content of the above identified application is incorporated herein by reference.

Some references, which may include patents, patent applications and various publications, may be cited and discussed in the description of this disclosure. The citation and/or discussion of such references is provided merely to clarify the description of the present disclosure and is not an admission that any such reference is "prior art" to the disclosure described herein. All references cited and discussed in this specification are incorporated herein by reference in their entireties and to the same extent as if each reference was individually incorporated by reference.

FIELD OF THE DISCLOSURE

The present disclosure relates to a ventilator system and a medical gas delivery system, and more particularly to a ventilator system and a medical gas delivery system that can be used to treat various diseases (especially for new coronary pneumonia or similar diseases).

BACKGROUND OF THE DISCLOSURE

Recently, with the rapid spread of the new coronary pneumonia epidemic, a large number of patients have been reported all over the world. For mild patients, symptoms can be controlled by using oxygen, hydroxychloroquine, remdesivir, or other medicine. When the conditions are improved, the mild patients can recuperate at home on their own. However, for moderate or severe patents, antibiotics or steroids need to be taken. Once respiratory failure occurs, use of a ventilator is required for treatment. Therefore, there is an increasing demand for the ventilator in each country.

A conventional ventilator supplies a medical gas through a gas cylinder, so as to provide an appropriate amount of oxygen to the patients and maintain respiration of the patients. However, when the ventilator is used in cooperation with the gas cylinder, the ventilator cannot be easily moved. In addition, a component of the gas cylinder is unitary, such that a component ratio of the medical gas cannot be adjusted arbitrarily.

As such, each time there is a change of the patient, the gas cylinder connected with the conventional ventilator needs to be replaced or combined with other gas cylinders in response to the disease of said patient, thereby causing use inconvenience.

In the related art, studies have shown that hydrogen can be used to treat diseases such as diabetes, hypertension, dementia, Parkinson's disease, depression, stroke, and myocardial infarction, and more particularly can be used to treat new coronary pneumonia or similar diseases. Studies have also shown that a mixed gas of hydrogen and oxygen can be used to treat new coronary pneumonia or similar diseases. Furthermore, ozone can be used to treat tuberculosis, anemia, allergic rhinitis, pneumonia, diabetes, gout, as well as new coronary pneumonia or similar diseases. While oxygen can be used to treat hypoxia, chronic obstructive pulmonary disease, or cystic fibrosis, a mixed gas of ozone and oxygen can be used to treat new coronary pneumonia or similar diseases.

In order to achieve a better therapeutic effect, multiple gases are mixed to be used as the medical gas. The conventional ventilator that is connected with the gas cylinder has problems of inconvenience in use and difficulty in adjusting the component ratio of the medical gas, and thus still has room for improvement.

SUMMARY OF THE DISCLOSURE

In response to the above-referenced technical inadequacies, the present disclosure provides a ventilator system and a medical gas delivery system.

In one aspect, the present disclosure provides a medical gas delivery system. The medical gas delivery system includes an electrolytic gas generation device, a delivery device, and a control unit. The electrolytic gas generation device is used to generate a first gas and a second gas. The delivery device is in fluid communication with the electrolytic gas generation device, and is used to transport a medical gas. The medical gas includes at least one of the first gas and the second gas. The control unit is electrically connected with the electrolytic gas generation device and the delivery device, so as to control a component ratio of the medical gas.

In certain embodiments, the control unit controls an electrolysis voltage of the electrolytic gas generation device. When the electrolysis voltage is lower than a predetermined voltage, the first gas is oxygen and the second gas is hydrogen.

In certain embodiments, the control unit controls an electrolysis voltage of the electrolytic gas generation device. When the electrolysis voltage is higher than or equal to a predetermined voltage, the first gas is a mixed gas of oxygen and ozone and the second gas is hydrogen.

In certain embodiments, the delivery device includes a first gas storage unit and a second gas storage unit. The first gas storage unit is in fluid communication with the electrolytic gas generation device and is used to store the first gas. The second gas storage unit is in fluid communication with the electrolytic gas generation device and is used to store the second gas.

In certain embodiments, the first gas storage unit includes a first storage tank and a first gas sensor. The first storage tank is used to store the first gas. The first gas sensor is used to detect first concentration detection data in the first storage tank. The second gas storage unit includes a second storage tank and a second gas sensor. The second storage tank is used to store the second gas. The second gas sensor is used to detect a second concentration detection data in the second storage tank. The control unit adjusts the component ratio of the medical gas according to the first concentration detection data and the second concentration detection data.

In certain embodiments, the delivery device includes a first channel, a second channel, a confluence channel, a first control valve, and a second control valve. The first channel is in fluid communication with the first gas storage unit so as to deliver the first gas. The second channel is in fluid communication with the second gas storage unit so as to deliver the second gas. The confluence channel is in fluid communication with the first channel and the second channel so as to deliver the medical gas. The first control valve is mounted on the first channel and electrically connected with the control unit, so as to control the discharge of the first gas or deliver the first gas to the confluence channel. The second control valve is mounted on the second channel and electrically connected with the control unit, so as to control the discharge of the second gas or deliver the second gas to the confluence channel.

In certain embodiments, the electrolytic gas generation device includes a membrane electrode assembly, an adjustable power supply, and an electrolysis tank. The membrane electrode assembly is electrically connected with the adjustable power supply. The membrane electrode assembly is disposed in the electrolysis tank.

In certain embodiments, the membrane electrode assembly includes an anode, a cathode, and a proton exchange membrane disposed between the anode and the cathode. The anode is used to generate the first gas, and the cathode is used to generate the second gas.

In certain embodiments, the medical gas is selected from the group consisting of: hydrogen, oxygen, a mixed gas of hydrogen and oxygen, a mixed gas of oxygen and ozone, and a mixed gas of hydrogen, oxygen, and ozone.

In certain embodiments, the medical gas delivery system is applied in a ventilator system, an intravenous system, a rectal insufflation system, or a blood treatment system.

In certain embodiments, the medical gas is used to treat coronary pneumonia or similar diseases. The medical gas delivery system is applied in at least two of a ventilator system, an intravenous system, a rectal insufflation system, and a blood treatment system.

In another aspect, the present disclosure provides a ventilator system. The ventilator system includes the medical gas delivery system and a gas supply device. The gas supply device is in fluid communication with the delivery device. The gas supply device is used to provide the medical gas to a patient and receive exhaled gas from the patient.

In certain embodiments, the ventilator system further includes a detector disposed in the gas supply device. A pressure of the medical gas and a pressure of the exhaled gas are detected by the detector so as to obtain pressure detection data. The control unit adjusts, according to the pressure detection data fed back by the detector, at least one of the component ratio of the medical gas and a delivery pressure value of the medical gas.

In certain embodiments, the ventilator system further includes a humidifier in fluid communication with the gas supply device. The medical gas is subjected to a humidifying process before being delivered to a lung of the patient.

In certain embodiments, the ventilator system is used to treat coronary pneumonia or similar diseases.

In certain embodiments, the medical gas delivery system is further connected and used with at least one of an intravenous system, a rectal insufflation system, and a blood treatment system.

Therefore, in the ventilator system and the medical gas delivery system provided by the present disclosure, by virtue of "the electrolytic gas generation device being used to generate a first gas and a second gas" and "the control unit being electrically connected with the electrolytic gas generation device and the delivery device, so as to control a component ratio of the medical gas," the convenience of using a ventilator can be enhanced.

These and other aspects of the present disclosure will become apparent from the following description of the embodiment taken in conjunction with the following drawings and their captions, although variations and modifications therein may be affected without departing from the spirit and scope of the novel concepts of the disclosure.

4

BRIEF DESCRIPTION OF THE DRAWINGS

The described embodiments may be better understood by reference to the following description and the accompanying drawings, in which.

DETAILED DESCRIPTION OF THE EXEMPLARY EMBODIMENTS

Figure 1:
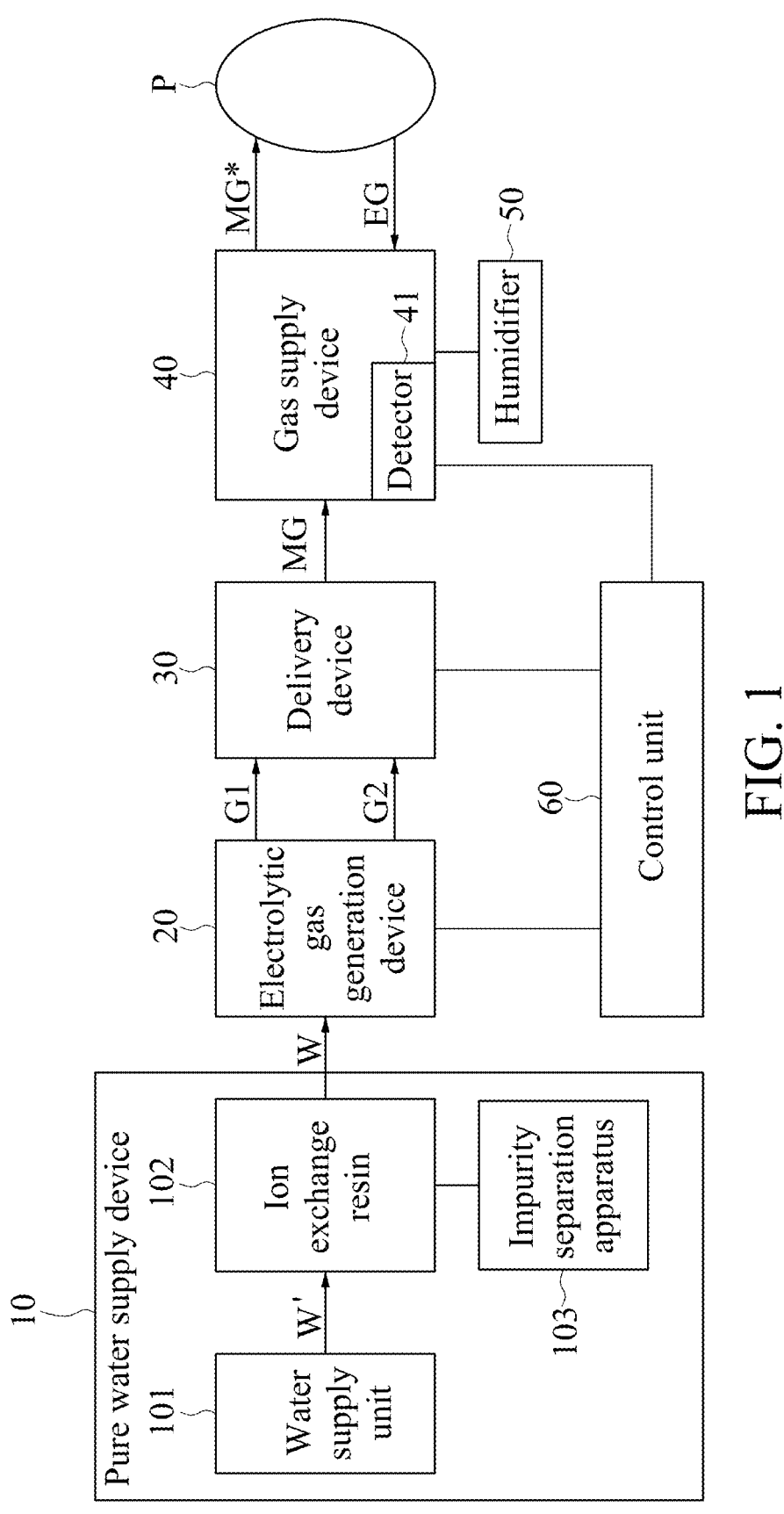
FIG. 1 is a functional block diagram of a ventilator system according to the present disclosure.

The present disclosure is more particularly described in the following examples that are intended as illustrative only since numerous modifications and variations therein will be apparent to those skilled in the art. Like numbers in the drawings indicate like components throughout the views. As used in the description herein and throughout the claims that follow, unless the context clearly dictates otherwise, the meaning of "a", "an", and "the" includes plural reference, and the meaning of "in" includes "in" and "on". Titles or subtitles can be used herein for the convenience of a reader, which shall have no influence on the scope of the present disclosure.

The terms used herein generally have their ordinary meanings in the art. In the case of conflict, the present document, including any definitions given herein, will prevail. The same thing can be expressed in more than one way. Alternative language and synonyms can be used for any term(s) discussed herein, and no special significance is to be placed upon whether a term is elaborated or discussed herein. A recital of one or more synonyms does not exclude the use of other synonyms. The use of examples anywhere in this specification including examples of any terms is illustrative only, and in no way limits the scope and meaning of the present disclosure or of any exemplified term. Likewise, the present disclosure is not limited to various embodiments given herein. Numbering terms such as "first", "second" or "third" can be used to describe various components, signals or the like, which are for distinguishing one component/signal from another one only, and are not intended to, nor should be construed to impose any substantive limitations on the components, signals or the like.

In order to improve the inconvenience of using a conventional ventilator, the present disclosure provides a ventilator system and a medical gas delivery system. The ventilator system and the medical gas delivery system of the present disclosure include an electrolytic gas generation device. The electrolytic gas generation device generates gases (i.e., hydrogen, oxygen, and ozone) by water electrolysis. A medical gas can be formed through selection or combination of the gases, and can be directly provided to patients.

Hydrogen is conventionally generated by using natural gas as a raw material and through reformation. However, a system of hydrogen reformation is complicated. In addition to hydrogen, carbon monoxide (which is harmful to the human body) is also included in a final product, such that the final product is not suitable to be used as the medical gas.

Oxygen is conventionally generated by using air as a raw material and through air separation. However, a system of the air separation is complicated and noises are produced during the air separation, such that this system is not suitable for use when the patients need to rest.

Ozone is conventionally generated by applying a high voltage onto two electric plates for simulation of a lightning strike phenomenon (a corona method). When oxygen is excited by electrons, energy can be obtained and ozone can be generated after collision of oxygen. However, nitrogen oxides (which are suspected to be carcinogenic) are also generated during the corona method.

Therefore, compared to the natural gas reformation (for producing hydrogen), the air separation (for producing oxygen), and the corona method (for producing ozone) in the related art, the gases are generated through electrolysis in the present disclosure. In this way, the convenience in use is much improved. In addition, the gases produced in the present disclosure have a higher quality.

Referring to FIG. 1, FIG. 1 shows a functional block diagram of a ventilator system according to the present disclosure. The ventilator system of the present disclosure can provide hydrogen, oxygen, ozone (mixed with oxygen) or any mixed gas according to practical medical uses.

The ventilator system of the present disclosure includes a pure water supply device 10, an electrolytic gas generation device 20, a delivery device 30, an gas supply device 40, a humidifier 50, and a control unit 60.

The pure water supply device 10 is used to provide pure water W. The pure water supply device 10 includes a water supply unit 101, an ion exchange resin 102, and an impurity separation apparatus 103. Water W' provided by the water supply unit 101 passes through the ion exchange resin 102 and the impurity separation apparatus 103, so that anion ions, cation ions, and impurities dissolved in the water can be removed and the pure water W can be obtained.

The pure water W provided by the pure water supply device 10 is electrolyzed by the electrolytic gas generation device 20, so as to generate a first gas G1 and a second gas G2. In the present embodiment, the first gas G1 is oxygen or a mixed gas of oxygen and ozone, and the second gas G2 is hydrogen.

Figure 2:
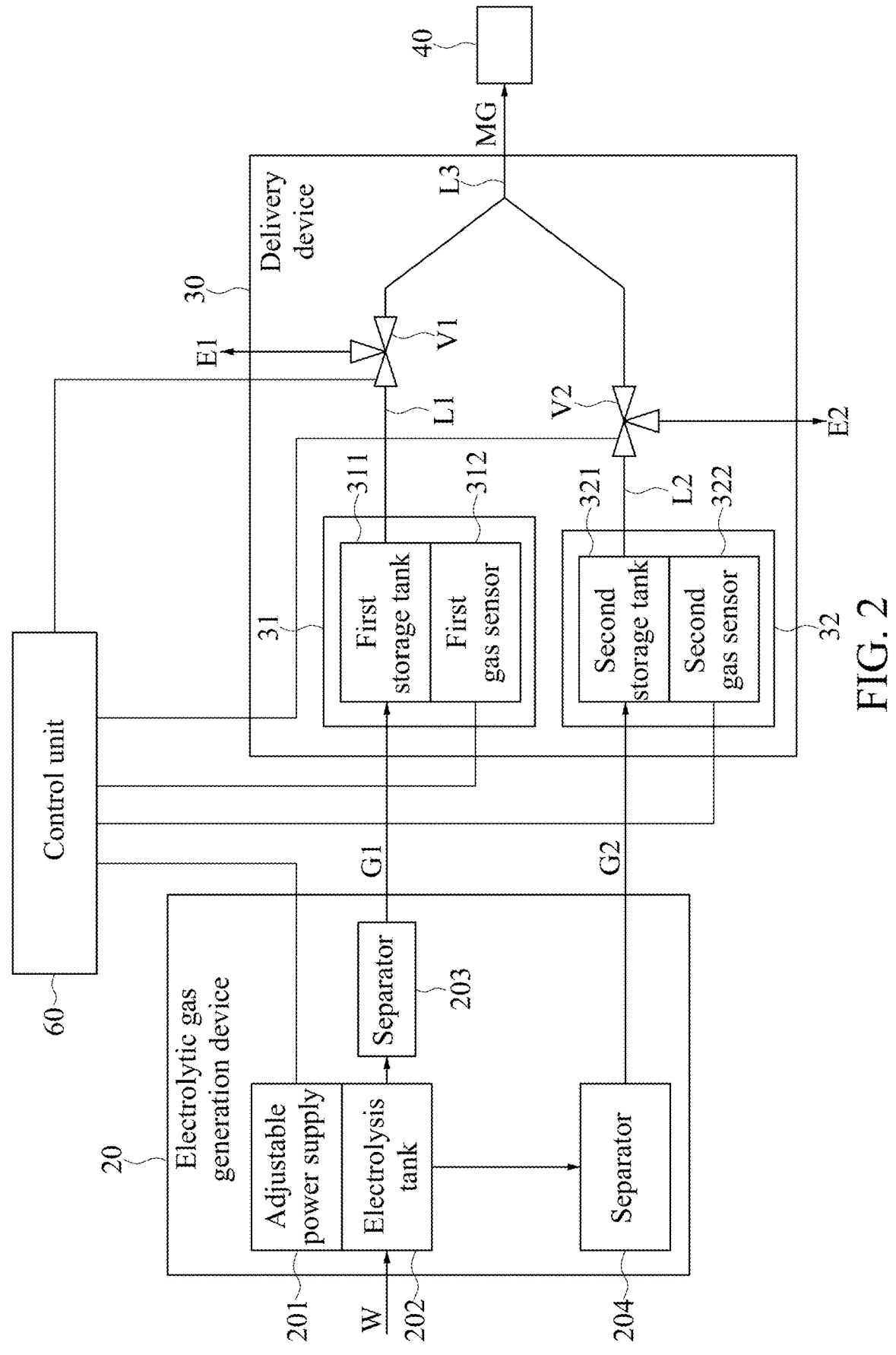
FIG. 2 is a functional block diagram of an electrolytic gas generation device and a delivery device according to the present disclosure.

In the present embodiment, the electrolytic gas generation device 20 is a proton exchange membrane (PEM) electrolytic gas generation device. Referring to FIG. 2, FIG. 2 shows a functional block diagram of an electrolytic gas generation device and a delivery device according to the present disclosure. Specifically, the electrolytic gas generation device 20 includes an adjustable power supply 201, an electrolysis tank 202, and separators 203, 204. The adjustable power supply 201 provides power for electrolysis. The electrolysis tank 202 is in fluid communication with the pure water supply device 10, so as to receive the pure water W provided by the pure water supply device 10. The separators 203, 204 are used to separate the gases from water in the electrolysis tank 202 generated after the electrolysis.

Figure 3:
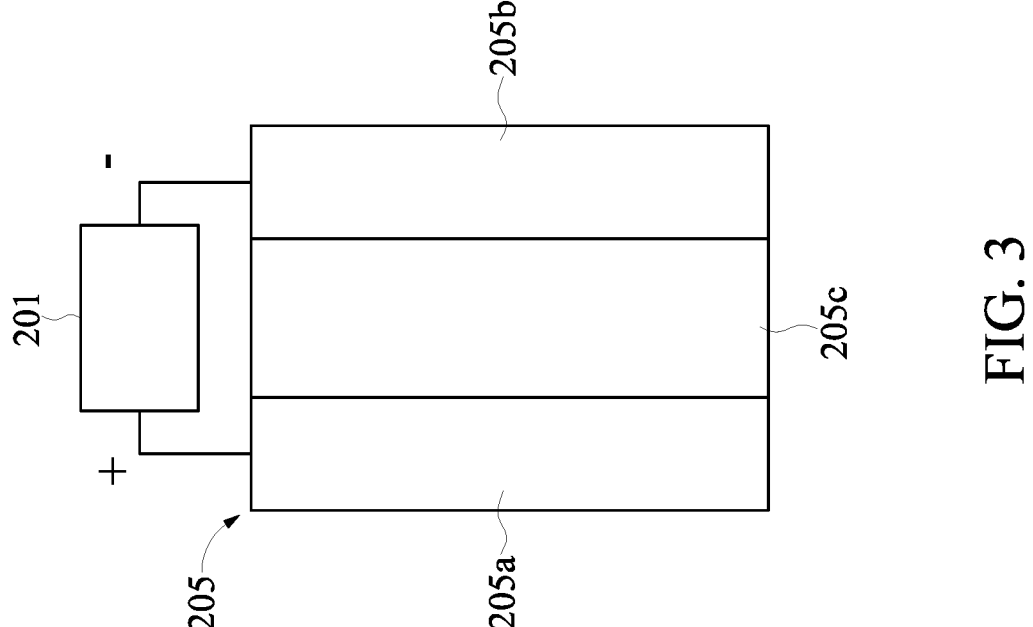
FIG. 3 is a schematic view of a membrane electrode assembly according to the present disclosure.

It should be noted that the electrolytic gas generation device 20 includes a membrane electrode assembly 205. Referring to FIG. 3, FIG. 3 shows a schematic view of a membrane electrode assembly according to the present disclosure. The membrane electrode assembly 205 includes an anode 205a, a cathode 205b, and a proton exchange membrane 205c disposed between the anode 205a and the cathode 205b.

The membrane electrode assembly 205 is disposed in the electrolysis tank 202, and is electrically connected with the adjustable power supply 201. Specifically, the anode 205a is electrically connected with a positive electrode of the adjustable power supply 201, and the cathode 205b is electrically connected with a negative electrode of the adjustable power supply 201.

During the electrolysis, an electrolysis voltage is applied onto the membrane electrode assembly 205 by the adjustable power supply 201, so as to electrolyze the pure water W in the electrolysis tank 202. Accordingly, the first gas G1 is generated by the anode 205a, and the second gas G2 is generated by the cathode 205b.

Specifically, when the electrolysis voltage applied by the adjustable power supply 201 is lower than a predetermined voltage, the first gas G1 is oxygen, and the second gas G2 is hydrogen. When the electrolysis voltage applied by the adjustable power supply 201 is higher than or equal to the predetermined voltage, the first gas G1 is a mixed gas of oxygen and ozone, and the second gas G2 is hydrogen. In an exemplary embodiment, the predetermined voltage is 3.0 V.

Further, when the first gas G1 contains oxygen and ozone, a concentration ratio of oxygen and ozone is also related to the electrolysis voltage. As the electrolysis voltage increases, a concentration of ozone in the first gas G1 also increases. For example, when the electrolysis voltage ranges from 3.0 V to 3.8 V, the first gas G1 contains an appropriate amount of ozone. When the electrolysis voltage ranges from 3.8 V to 10.0 V, the amount of ozone in the first gas G1 can further increase.

In addition to the electrolysis voltage, components of the first gas G1 can also be affected by the type of a catalyst layer coated on the anode 205a. When a material of the anode 205a includes iridium, iridium black, iridium dioxide, ruthenium, ruthenium oxide, platinum, platinum iridium, palladium, iridium ruthenium oxide, iridium ruthenium tantalum oxide, or any combination thereof, generation of oxygen is facilitated. Preferably, the material of the anode 205a includes iridium dioxide. When the material of the anode 205a includes tin-antimony-nickel alloy, lead dioxide, glassy carbon, boron-doped diamond, platinum-tantalum oxide, or any combination thereof, simultaneous generation of oxygen and ozone is facilitated. Preferably, the material of the anode 205a includes lead dioxide.

In the present embodiment, the material of the anode 205a and the electrolysis voltage applied onto the membrane electrode assembly 205 can be adjusted according to desired components of the first gas G1. A material of the cathode 205b can be platinum (Pt)/carbon black coated on a carbon cloth. No matter how the electrolysis voltage or the material of the cathode 205b is adjusted, the second gas G2 generated by the cathode 205b is always hydrogen.

It should be noted that hydrogen, oxygen, and ozone are able to be mixed with water vapor after the electrolysis. Therefore, the separators 203, 204 are needed for separation of the water vapor, so as to obtain the first gas G1 and the second gas G2.

Referring to FIG. 1 and FIG. 2, the delivery device 30 is in fluid communication with the electrolytic gas generation device 20. The delivery device 30 receives the first gas G1 and the second gas G2 generated by the electrolytic gas generation device 20, and the delivery device 30 is used to transport a medical gas MG. According to the first gas G1 and the second gas G2 that the delivery device 30 receives, the medical gas MG is selectively formed. In other words, the medical gas MG includes at least one of the first gas G1 and the second gas G2.

Based on the descriptions mentioned above, the first gas G1 is the mixed gas of oxygen and ozone, and the second gas G2 is hydrogen. Therefore, the medical gas MG is selected from the group consisting of: hydrogen, oxygen, a mixed gas of hydrogen and oxygen, a mixed gas of oxygen and ozone, and a mixed gas of hydrogen, oxygen, and ozone. The medical gas MG can be used to treat various diseases, which include diseases that can be treated by at least one of hydrogen, oxygen, and ozone (e.g., diseases related to new coronary pneumonia). However, the present disclosure is not limited thereto.

The delivery device 30 includes a first gas storage unit 31 and a second gas storage unit 32. The first gas storage unit 31 is in fluid communication with the electrolytic gas generation device 20 and stores the first gas G1 generated by the anode 205*a*. The second gas storage unit 32 is in fluid communication with the electrolytic gas generation device 20 and stores the second gas G2 generated by the cathode 205*b*.

The first gas storage unit 31 includes a first storage tank 311 and a first gas sensor 312. The first gas G1 is stored in the first storage tank 311. The first gas sensor 312 is disposed in the first storage tank 311, so as to detect the first concentration detection data (such as a concentration of oxygen and ozone) in the first storage tank 311. The first gas sensor 312 is electrically connected with the control unit 60, so as to transfer the first concentration detection data to the control unit 60 at any time.

Similarly, the second gas storage unit 32 includes a second storage tank 321 and a second gas sensor 322. The second gas G2 is stored in the second storage tank 321. The second gas sensor 322 is disposed in the second storage tank 321, so as to detect second concentration detection data (such as a concentration of hydrogen) in the second storage tank 321. The second gas sensor 322 is electrically connected with the control unit 60, so as to transfer the second concentration detection data to the control unit 60 at any time.

The delivery device 30 further includes a first channel L1, a second channel L2, a confluence channel L3, a first control valve V1, and a second control valve V2. The first channel L1 is in fluid communication with the first storage tank 311, so as to deliver the first gas G1. The second channel L2 is in fluid communication with the second storage tank 321, so as to deliver the second gas G2. The confluence channel L3 is in fluid communication with the first channel L1 and the second channel L2, so as to deliver the medical gas MG. The first control valve V1 is disposed on the first channel L1 and is electrically connected with the control unit 60, so as to selectively discharge the first gas G1 through a first exit E1 or selectively deliver the first gas G1 to the confluence channel L3. The second control valve V2 is disposed on the second channel L2 and is electrically connected with the control unit 60, so as to selectively discharge the second gas G2 through a second exit E2 or selectively deliver the second gas G2 to the confluence channel L3.

The control unit 60 is electrically connected with the electrolytic gas generation device 20 and the delivery device 30. Specifically, the control unit 60 is electrically connected with the adjustable power supply 201, the first control valve V1, and the second control valve V2. In addition, the control unit 60 can receive the first concentration detection data fed back by the first gas sensor 312 and the second concentration detection data fed back by the second gas sensor 322. According to the first concentration detection data and the second concentration detection data, the control unit 60 can adjust the electrolysis voltage applied onto the membrane electrode assembly 205 by the adjustable power supply 201, and valves of the first control valve V1 and the second control valve V2 can also be controlled and turned. Therefore, the component ratio of the medical gas MG can be controlled by the control unit 60.

The pure water supply device 10, the electrolytic gas generation device 20, the delivery device 30, and the control unit 60 mentioned above are collectively referred to as the medical gas delivery system. The medical gas delivery system of the present disclosure can be applied in the ventilator system, so as to replace a gas cylinder used in the conventional ventilator.

In addition, according to practical requirements, the medical gas delivery system of the present disclosure can also be applied in an intravenous system or a rectal insufflation system. For example, when ozone is used in a treatment process, a concentration of ozone that can be inhaled through the nasal cavity has an upper limit and cannot be arbitrarily increased. Accordingly, ozone with a high concentration can be introduced into the human body via a vein or a rectum, so as to achieve a desired therapeutic effect.

In one embodiment of the present disclosure, the medical gas delivery system is used to treat new coronary pneumonia or similar diseases. Therefore, the medical gas delivery system can be applied in the ventilator system and at least one of the intravenous system and the rectal insufflation system at the same time. Hydrogen and oxygen can be injected through the ventilator system, and ozone (mixed with oxygen) can be injected through the intravenous system and/or the rectal insufflation system, so as to achieve a better therapeutic effect. In other words, the medical gas delivery system of the present disclosure can be applied in at least two of the ventilator system, the intravenous system, and the rectal insufflation system. The first gas G1 and/or the second gas G2 can be delivered to the gas supply device 40 via the delivery device 30 of the medical gas delivery system, and then can be introduced into the human body by different ways.

In an exemplary embodiment, the medical gas delivery system of the present disclosure can be simultaneously applied in the ventilator system and the intravenous system, or can be simultaneously applied in the ventilator system and the rectal insufflation system. However, the present disclosure is not limited thereto.

In addition to injecting the medical gas MG into the human body, the medical gas delivery system of the present disclosure can also be applied in extracorporeal treatments, such as autohemotherapy.

The medical gas delivery system of the present disclosure can also be applied in a blood treatment system. Specifically, blood is first drawn from a vein of the patient. When the blood is in contact with ozone, viruses and bacteria in the blood can be killed and activity of immune cells in the blood can be enhanced. Then, the processed blood is reinjected into the human body, such that a recuperative effect can be achieved through the patient's own blood.

The gas supply device 40 is in fluid communication with the delivery device 30. The gas supply device 40 is used to provide the medical gas MG that is generated by the delivery device 30. Further, the gas supply device 40 can also be used to receive exhaled gas EG from the patient P.

A detector 41 is disposed in the gas supply device 40. The detector 41 can be used to detect pressure detection data (such as a pressure value and a gas flow) of the medical gas MG and the exhaled gas EG. The detector 41 is electrically connected with the control unit 60, so as to transfer the pressure detection data to the control unit 60. According to the pressure detection data, the control unit 60 can evaluate whether the patient is spontaneously breathing and determine whether a delivery pressure value of the medical gas MG or the component ratio of the medical gas MG needs to be adjusted.

The medical gas MG is injected into the patient's lung by the gas supply device 40, and the exhaled gas EG from the patient P_is received by the gas supply device 40. Generally, the gas supply device 40 exerts a positive pressure to inject the medical gas MG into the patient's lung. Once the gas supply device 40 exerts no pressure, a pressure in the patient's lung is higher than a surrounding pressure. Then, the patient P exhales the exhaled gas EG, so that a pressure balance inside and outside the patient's body can be reached.

If the patient can spontaneously breathe after the treatment, a pressure difference will be formed between the medical gas MG and the exhaled gas EG. At this time, upon receipt of the pressure detection data, the control unit 60 determines whether an amount of the medical gas MG needs to be decreased and whether the first control valve V1 and the second control valve V2 need to be adjusted, so as to deliver the medical gas MG with an appropriate pressure value.

When spontaneous breathing efforts of the patient are low, the medical gas MG can be hydrogen, oxygen, the mixed gas of hydrogen and oxygen, the mixed gas of oxygen and ozone, or the mixed gas of hydrogen, oxygen, and ozone (which have a therapeutic effect). When the spontaneous breathing efforts of the patient are high, the component ratio of the medical gas MG can be adjusted to oxygen or the mixed gas of hydrogen and oxygen (either of which has a health care effect).

In some embodiments, the gas supply device 40 is used in cooperation with a humidifier 50. The medical gas MG can be humidified by the humidifier 50, so that a temperature of the medical gas MG is closer to a temperature of the human body and a humidity of the medical gas MG can be increased. A humidified medical gas MG* that is treated by the humidifier 50 can be provided to the patients via medical tubes for breathing purposes.

Beneficial Effects of the Embodiments

In conclusion, in the ventilator system and the medical gas delivery system provided by the present disclosure, by virtue of "the electrolytic gas generation device being used to generate a first gas and a second gas" and "the control unit being electrically connected with the electrolytic gas generation device and the delivery device, so as to control a component ratio of the medical gas," the usability of the ventilator can be enhanced.

Further, by virtue of "the first gas being oxygen and the second gas being hydrogen when the electrolysis voltage being lower than a predetermined voltage" or "the first gas being a mixed gas of oxygen and ozone and the second gas being hydrogen when the electrolysis voltage being higher than or equal to a predetermined voltage," the therapeutic effect of the ventilator can be enhanced.

Further, by virtue of "the control unit adjusting the component ratio of the medical gas according to the first concentration detection data and the second concentration detection data," the therapeutic effect of the ventilator can be enhanced.

Further, by virtue of "the control unit adjusting, according to the pressure detection data fed back by the detector, at least one of the component ratio of the medical gas and a delivery pressure value of the medical gas," the therapeutic effect of the ventilator can be enhanced.

The foregoing description of the exemplary embodiments of the disclosure has been presented only for the purposes of illustration and description and is not intended to be exhaustive or to limit the disclosure to the precise forms disclosed. Many modifications and variations are possible in light of the above teaching.

The embodiments were chosen and described in order to explain the principles of the disclosure and their practical application so as to enable others skilled in the art to utilize the disclosure and various embodiments and with various modifications as are suited to the particular use contemplated. Alternative embodiments will become apparent to those skilled in the art to which the present disclosure pertains without departing from its spirit and scope.

What is claimed is:

1. A medical gas delivery system, comprising:
an electrolytic gas generation device used to generate a first gas and a second gas,
wherein the electrolytic gas generation device includes a membrane electrode assembly, an electrolysis tank, a first separator, and a second separator,
wherein the membrane electrode assembly is disposed in the electrolysis tank, the membrane electrode assembly includes an anode, and a material of the anode includes iridium dioxide,
wherein the first separator is in fluid communication with the electrolysis tank and is configured to separate the first gas from water in the electrolysis tank generated after an electrolysis, and
wherein the second separator is in fluid communication with the electrolysis tank and is configured to separate the second gas from water in the electrolysis tank generated after the electrolysis;
a delivery device, wherein the delivery device is in fluid communication with the electrolytic gas generation device, and the delivery device is used to deliver a medical gas; wherein the medical gas includes at least one of the first gas and the second gas; and
a control unit electrically connected with the electrolytic gas generation device and the delivery device, so as to control a component ratio of the medical gas.

2. The medical gas delivery system according to claim 1, wherein the control unit controls an electrolysis voltage of the electrolytic gas generation device; wherein, when the electrolysis voltage is lower than a predetermined voltage, the first gas is oxygen and the second gas is hydrogen.

3. The medical gas delivery system according to claim 1, wherein the control unit controls an electrolysis voltage of the electrolytic gas generation device; wherein, when the electrolysis voltage is higher than or equal to a predetermined voltage, the first gas is a mixed gas of oxygen and ozone and the second gas is hydrogen.

4. The medical gas delivery system according to claim 1, wherein the delivery device includes:
a first gas storage unit, wherein the first gas storage unit is in fluid communication with the electrolytic gas generation device, and is used to store the first gas; and
a second gas storage unit, wherein the second gas storage unit is in fluid communication with the electrolytic gas generation device, and is used to store the second gas.

5. The medical gas delivery system according to claim 4, wherein the first gas storage unit includes a first storage tank and a first gas sensor, the first storage tank is used to store the first gas, and the first gas sensor is used to detect first concentration detection data in the first storage tank; wherein the second gas storage unit includes a second storage tank and a second gas sensor, the second storage tank is used to store the second gas, and the second gas sensor is used to detect second concentration detection data in the second storage tank; wherein the control unit adjusts the component ratio of the medical gas according to the first concentration detection data and the second concentration detection data.

6. The medical gas delivery system according to claim 4, wherein the delivery device includes:

a first channel, wherein the first channel is in fluid communication with the first gas storage unit, so as to deliver the first gas;

a second channel, wherein the second channel is in fluid communication with the second gas storage unit, so as to deliver the second gas;

a confluence channel, wherein the confluence channel is in fluid communication with the first channel and the second channel, so as to deliver the medical gas;

a first control valve mounted on the first channel and electrically connected with the control unit, so as to control a discharge of the first gas or deliver the first gas to the confluence channel; and a second control valve mounted on the second channel and electrically connected with the control unit, so as to control a discharge of the second gas or deliver the second gas to the confluence channel.

7. The medical gas delivery system according to claim 1, wherein the electrolytic gas generation device includes an adjustable power supply, and the membrane electrode assembly is electrically connected with the adjustable power supply.

8. The medical gas delivery system according to claim 7, wherein the membrane electrode assembly includes a cathode, and a proton exchange membrane disposed between the anode and the cathode, the anode is used to generate the first gas, and the cathode is used to generate the second gas.

9. The medical gas delivery system according to claim 1, wherein the medical gas is selected from the group consisting of: hydrogen, oxygen, a mixed gas of hydrogen and oxygen, a mixed gas of oxygen and ozone, and a mixed gas of hydrogen, oxygen, and ozone.

10. The medical gas delivery system according to claim 1, wherein the medical gas is used to treat coronary pneumonia, and the medical gas delivery system is applied in a ventilator system.

11. A ventilator system, comprising:

the medical gas delivery system as claimed in claim 1;

a gas supply device, wherein the gas supply device is in fluid communication with the delivery device and the gas supply device is used to provide the medical gas to a patient and receive exhaled gas from the patient; and a detector disposed in the gas supply device, wherein the detector is configured to detect a pressure difference between the medical gas and the exhaled gas, and to generate a pressure detection data, wherein the control unit is electrically connected with the detector, and the control unit is configured to evaluate whether the patient is breathing spontaneously, based on the pressure detection data, and to adjust an electrolysis voltage of the electrolytic gas generation device, and wherein, when the electrolysis voltage is lower than a predetermined voltage, the first gas is oxygen and the second gas is hydrogen, and when the electrolysis voltage is higher than or equal to the predetermined voltage, the first gas is a mixed gas of oxygen and ozone and the second gas is hydrogen.

12. The ventilator system according to claim 11, further comprising a humidifier, wherein the humidifier is in fluid communication with the gas supply device, and the medical gas is subjected to a humidifying process before being delivered to a lung of the patient.

13. The ventilator system according to claim 11, wherein the ventilator system is used to treat coronary pneumonia.

* * * * *